(12) United States Patent
Levernier

(10) Patent No.: US 7,856,984 B2
(45) Date of Patent: Dec. 28, 2010

(54) SURGICAL COVERING MATERIAL

(75) Inventor: Jeffrey S. Levernier, Antioch, IL (US)

(73) Assignee: PPC Industries, Inc., Pleasant Prairie, WI (US)

( * ) Notice: Subject to any disclaimer, the term of this patent is extended or adjusted under 35 U.S.C. 154(b) by 623 days.

(21) Appl. No.: 11/643,590

(22) Filed: Dec. 21, 2006

(65) Prior Publication Data

US 2008/0149112 A1 Jun. 26, 2008

(51) Int. Cl.
*A61B 19/08* (2006.01)

(52) U.S. Cl. ................................ 128/853; 128/849

(58) Field of Classification Search .......... 128/849, 128/850, 851, 852, 853, 854, 855, 856
See application file for complete search history.

(56) References Cited

U.S. PATENT DOCUMENTS

| | | | |
|---|---|---|---|
| 3,300,366 A * | 1/1967 | Krolik, Jr. .................... 428/136 |
| 3,637,458 A | 1/1972 | Parrish ........................ 161/160 |
| 3,916,887 A * | 11/1975 | Kelly .......................... 128/851 |
| 5,143,091 A * | 9/1992 | Patnode et al. ............... 128/853 |
| 5,151,314 A | 9/1992 | Brown |
| 5,379,703 A | 1/1995 | Marshall ...................... 108/90 |
| 5,453,296 A * | 9/1995 | Lauritzen et al. .......... 427/208.6 |
| 5,546,960 A * | 8/1996 | Billgren ....................... 128/849 |
| 5,698,294 A * | 12/1997 | Van Hout et al. ............ 428/156 |
| 5,804,112 A | 9/1998 | Greene ....................... 264/45.9 |
| 5,871,015 A * | 2/1999 | Lofgren et al. .............. 128/849 |
| 5,901,706 A * | 5/1999 | Griesbach et al. ........... 128/849 |
| 6,105,579 A * | 8/2000 | Levitt et al. ................. 128/849 |
| 6,279,578 B1 * | 8/2001 | Hinley, Jr. .................. 128/849 |
| 6,694,981 B2 * | 2/2004 | Gingles et al. .............. 128/849 |
| 6,703,115 B2 | 3/2004 | Hale et al. ................... 428/212 |
| 6,748,952 B2 | 6/2004 | Hinley, Jr. |
| 6,809,048 B1 | 10/2004 | Jacobs ........................ 442/401 |
| 7,001,562 B2 | 2/2006 | Schiffer et al. .............. 264/491 |
| 7,078,089 B2 * | 7/2006 | Ellis et al. .................... 428/138 |
| 7,309,519 B2 * | 12/2007 | Scholz et al. ............... 428/119 |
| 2004/0166321 A1 * | 8/2004 | Rippl et al. ............. 428/411.1 |
| 2007/0113859 A1 * | 5/2007 | Allen et al. .................. 128/853 |

FOREIGN PATENT DOCUMENTS

WO 94/01051 A1 1/1994

OTHER PUBLICATIONS

3M™ Surgical Drapes and Gowns Selection Guide 2003-2004, Feb. 23, 2004, 3M Health Care / 3M Infection Protection.

* cited by examiner

*Primary Examiner*—Patricia M Bianco
*Assistant Examiner*—Ophelia Hawthorne
(74) *Attorney, Agent, or Firm*—David I. Roche; Baker & McKenzie LLP

(57) ABSTRACT

A surgical covering material formed by extruding a sheet, either by a blown film or a cast film process. The upper exposed layer of the material is made by using a foaming agent to create elongated depressions that are surrounded by raised areas. The alternating raised and depressed areas provide the material with a coefficient of friction that compares well to standard drape materials that include a non-woven layer. The raised and depressed areas also provide the material with hydrophilic and non-glare properties that make is a highly effective drape or covering material for use in making mayo stand covers, back table covers and patient drapes. The size and shape of the depressions may be varied to create materials of different toughness or tearability, and differing materials may be combined to form customized drapes with the ability to gain access or make pathways through the drape.

20 Claims, 4 Drawing Sheets

US 7,856,984 B2

SURGICAL COVERING MATERIAL

BACKGROUND AND SUMMARY OF THE INVENTION

The present invention relates to a surgical covering of the kind used to make, for example, mayo stand covers, back table covers and surgical drapes.

For years, surgical covers, including mayo stand covers, back table covers and surgical drapes have been made of a laminated sheet including a nonwoven fabric adhered to a plastic film. For example, surgical drapes such as those sold by 3M (its Steri-Drape 9000) consist of a laminate of polypropylene fibers and a polyethylene film. Similar drapes or coverings are sold by Amcor Ltd and by Pliant Corp. Nonwoven materials have been the preferred surface for surgical covers and drapes because of its frictional properties (i.e., instruments do not readily slip on nonwoven surfaces) and they have the benefit of being tough, non-glaring and hydrophilic.

Such laminates are relatively expensive to manufacture because of the additional cost of the nonwoven layer, and because there is an assembly step required by which the nonwoven must be connected to a film carrier layer. In addition, in some cases, fibers from the nonwoven layer (i.e., lint) may find their way into open wounds and may thereby adversely impact the sterility of the operating room environment. Finally, composites having a nonwoven upper layer are not easily ripped or opened up, and thus restrict a surgeon's ability to access areas of a patient's body in certain situations.

At least one manufacturer (see U.S. Pat. No. 6,748,952) has attempted to make a surgical cover from a film by embossing the film after it has been extruded. While this approach does have the benefit of eliminating the nonwoven layer, this solution is also expensive to manufacture because of the separate embossing step.

In some surgical drape applications, it is beneficial to allow the drape to be ripped from the edge or opened up to allow a surgeon to access an area of a patient previously covered. Nonwoven materials are generally quite tough and are not easily ripped or opened.

Thus, there is a need for a surgical cover made from cast or blown film that results in a sheet having a textured, hydrophilic exposed surface that is non-glaring and that has the beneficial features of a nonwoven surface with respect to its frictional properties, but without the adverse aspects of a non-woven layer, such as its additional cost, resistance to tearing, and its lint-forming characteristics. The surgical cover described below has these features and advantages.

BRIEF DESCRIPTION OF THE DRAWINGS

These and other features, aspects, objects, and advantages of the inventions described and claimed herein will become better understood upon consideration of the following detailed description, appended claims, and accompanying drawings where:

It should be understood that the drawings are not necessarily to scale and that the embodiments are sometimes illustrated by graphic symbols, phantom lines, diagrammatic representations and fragmentary views. In certain instances, details which are not necessary for an understanding of the inventions described and claimed herein or which render other details difficult to perceive may have been omitted. It should be understood, of course, that the inventions described herein are not necessarily limited to the particular embodiments illustrated herein.

DETAILED DESCRIPTION

Figure 1:
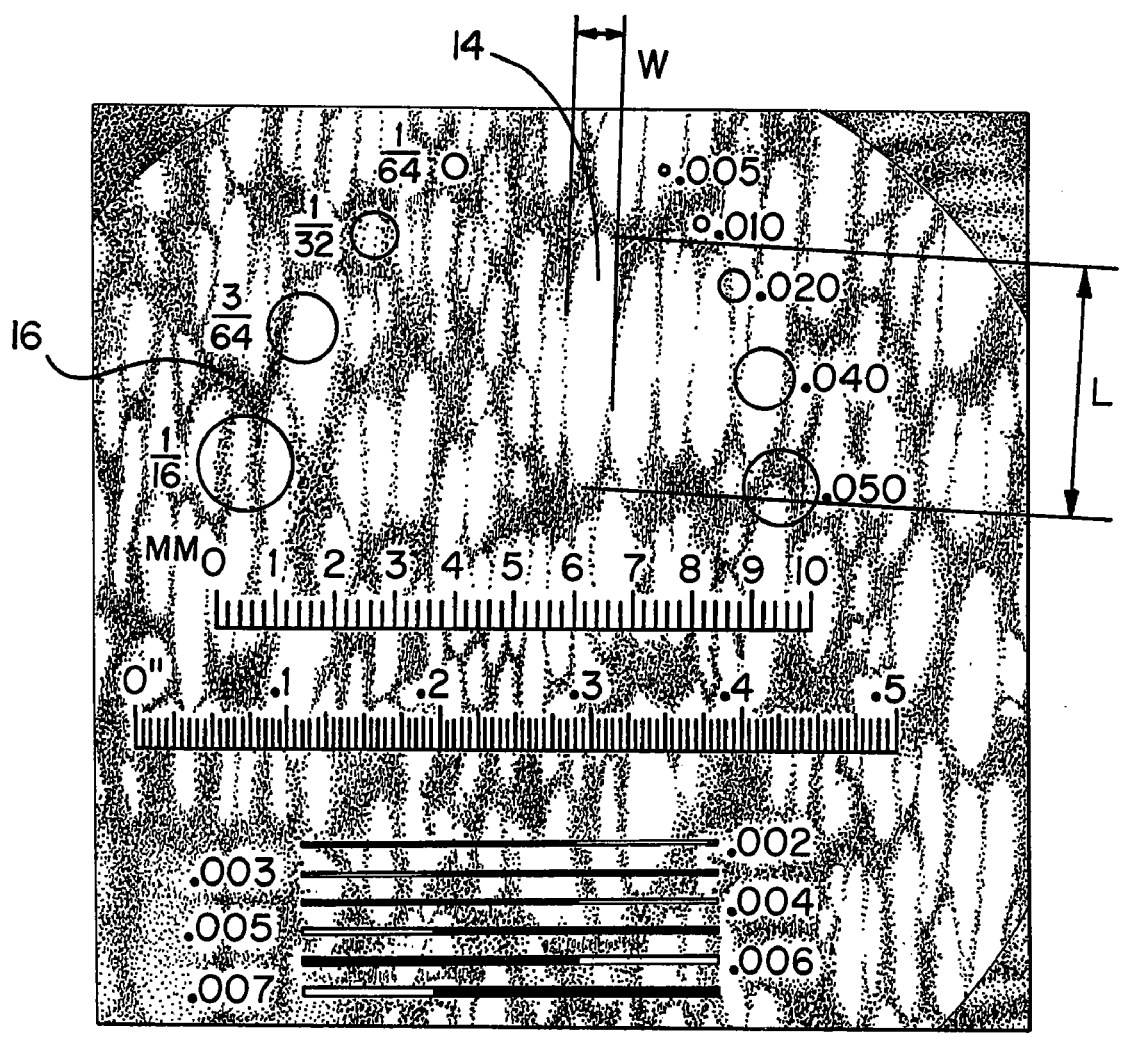
FIG. 1 is a close-up view of the surface properties of one example of a surgical cover made in accordance with the inventions claimed herein.
Figure 2:
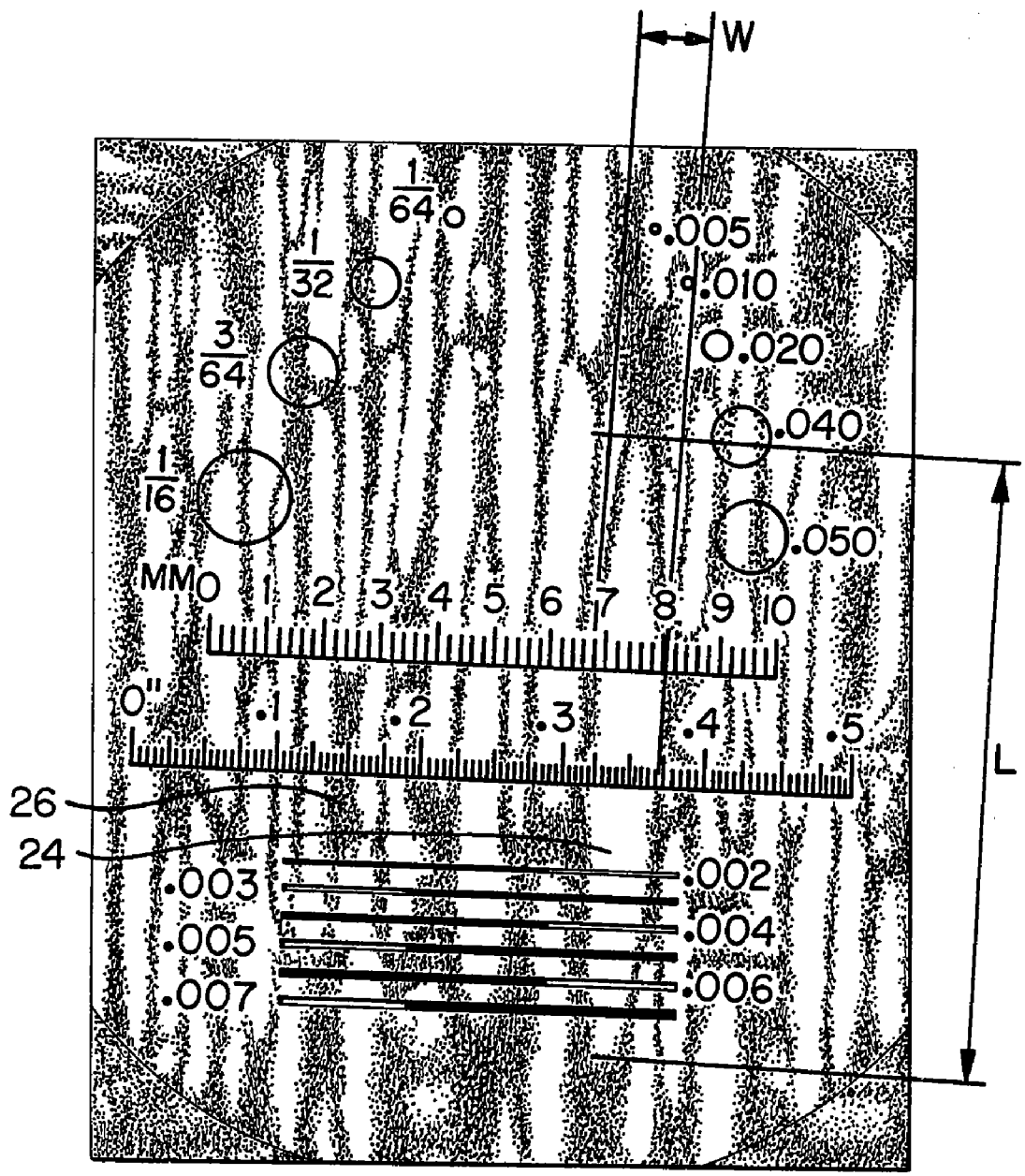
FIG. 2 is a close-up view of the surface properties of another example of a surgical cover made in accordance with the inventions claimed herein.

FIGS. 1 and 2 show two alternative embodiments of the surface of sheet material using the inventions claimed herein. The sheet 10 of FIG. 1 has surface depressions 14 that are elongated oval-like in shape and having length of up to about 0.135 inches. Between the oval-shaped depressions are raised areas 16. The oval-like depressions are non-uniform in size and have the appearance of being be randomly disposed, varying in length from very small (as small as 0.025 inches or even smaller) up to about 0.135. The larger depressions have a width of about 0.25 inches. This yields an aspect ratio (i.e., a ratio of length to width) of about 5.4 to 1.

In the FIG. 1 embodiment, the differences in elevation between the bottom of the depressions 14 and the maximum height of the raised areas 16 is about 2 mils in this particular example, wherein the gauge of the film without the foaming agent is 0.6 mils. The increase in apparent thickness of the layer is due to the inclusion of a foaming agent. However, the height difference will depend on several factors including the speed of extrusion, the amount of foaming agent used, and the type of material extruded.

FIG. 2 shows an embodiment wherein the depressions 24 are substantially more elongated than the depressions 14 in the embodiment of FIG. 1. As in FIG. 1, the embodiment of FIG. 2 has raised areas 26 that surround the depressions 24. The difference in the shape of the depressions of the FIG. 1 embodiment as compared to the FIG. 2 embodiment is the result of a different foaming agent, faster speed of extrusion and/or the amount of the foaming agent used. In both examples, the extrusion die openings for the three layers were the same, and the type of material used to form the middle and bottom layers were the same.

The two different embodiments shown in FIGS. 1 and 2 were made using two different grades of foaming agent. The material of FIG. 1 was made using foaming agent CFAC-5050 MT supplied by Polyfil Corporation, while the material of FIG. 2 was made using foaming agent ANC-0540-445 also supplied by Polyfil Corporation. In both cases, the same amount of foaming agent was used, i.e., up to about 2% by weight of the resin/agent mixture. The materials of FIGS. 1 and 2 were extruded using a blown film process at an extrusion speed of about 90 feet per minute. Thus, the only significant difference between process used to make the material of FIG. 1, as compared with FIG. 2, was the particular foaming agent used. This difference resulted in a product having a somewhat different color in that the material of FIG. 2 is somewhat darker that the FIG. 2 material.

In addition, and significant for purposes of its use as a surgical drape, the FIG. 2 material is much more easily torn in the direction of the extrusion than the material of FIG. 1. The material of FIG. 2 can be easily torn by hand, without the use of any tools and without the use of excessive force. The tear-ability of the material can be varied by altering the extrusion speed, although the range of speed may be limited to between 80 and 100 feet per minute. If the extrusion is performed too fast, sufficient foaming action will not occur and if it is performed too slow, the bubbles will pop. However the particular speed required will depend upon the results desired and upon the specific foaming agent and other materials used.

The depressions and adjacent raised portions are the result of the inclusion of a foaming agent in the feedstock of the plastic that is used in the process of extruding the sheet, and the depressions are the result of the stretching and bursting of bubbles formed by the foaming agent as the sheet leaves the extrusion die. The coefficient of friction (COF) provided by the use of the previously mentioned foaming agent gives results in terms of frictional properties that compare well to standard nonwoven drapes, as shown in the following table as measured by ASTM D-1894 (again, the particular results achieved will vary depending upon the particular materials and extrusion speed used to make the material):

| Material | Coefficient of Friction | | | |
| --- | --- | --- | --- | --- |
| | Metal to film (Kinetic) | Metal to film (Static) | Film to Film (Kinetic) | Film to Film (Static) |
| Embodiment of FIG. 1 | 0.365 | 0.390 | 0.425 | 0.490 |
| Nonwoven | 0.220 | 0.260 | 0.410 | 0.465 |

The depressions and adjacent raised portions also contribute to another beneficial property of the claimed invention, namely its hydrophilic property. While the particular materials used in the preferred embodiments do not necessarily absorb moisture, the surface texture of the material is believed to disturb the interfacial forces of liquid droplets which contact the surface of the material, thereby breaking the droplets up into smaller droplets which tend to wet out on the material's surface. Moreover, the smaller liquid droplets tend to "stick" within the depressions on surface of the material, such that flow of the smaller liquid droplets is inhibited. For example, the two preferred embodiments disclosed herein can retain water droplets with a diameter on the order of 1/16"-1/8", even when oriented in a vertical position. Such a property is desirable for surgical covering material to prevent moisture from contacting floor surfaces, thereby rendering the floor surfaces slippery, during surgery.

The surface depressions and adjacent raised portions also contribute to the non-glare characteristic of the claimed inventions. The surface roughness of the material tends to disperse light to reduce luminance and glare, thereby mitigating eye strain and fatigue during surgery. The textured surface of the claimed invention can be characterized as satin-like.

Figure 3:
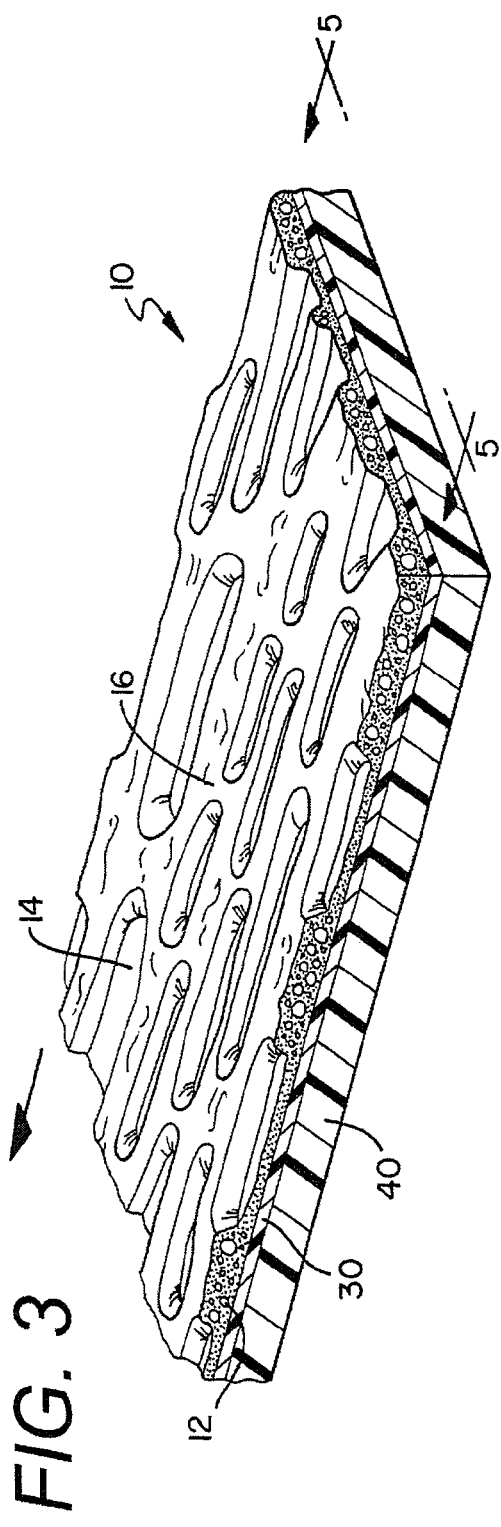
FIG. 3 is a perspective view showing the surface properties and a cross section of the surgical cover example of FIG. 1.
Figure 4:
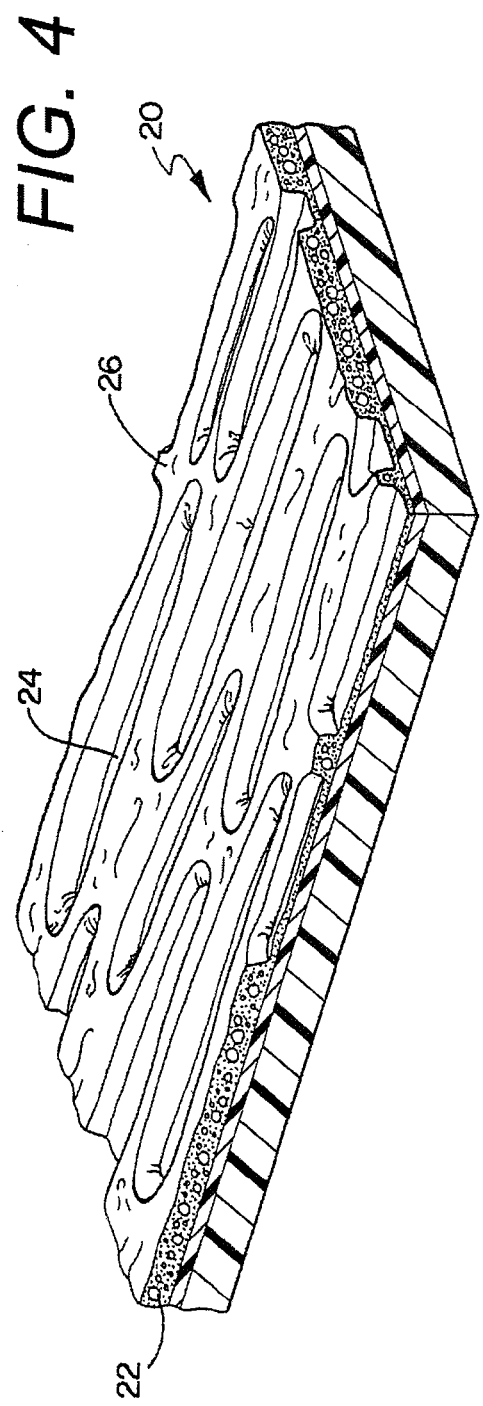
FIG. 4 is a perspective view showing the surface properties and a cross section of the surgical cover example of FIG. 2.
Figure 5:
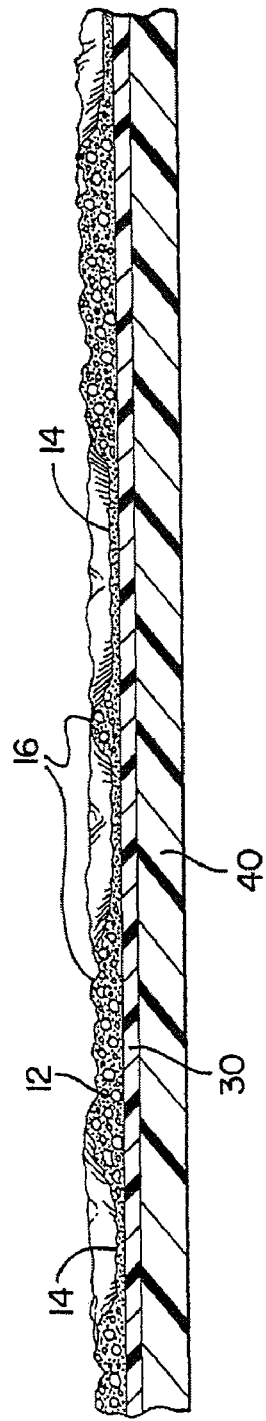
FIG. 5 is a cross-sectional view of an example of a surgical cover made in accordance with the inventions claimed herein.

The FIG. 1 embodiment was made using a blown film extrusion line with a foaming agent manufactured by Polyfil, i.e., its CFAC-5050 MT Chemical Foam Concentrate, added to a low linear density polyethylene resin as the outer textured layer. The FIG. 2 embodiment was made the same way, but with a different foaming agent also manufactured by Polyfil, i.e., its ANC-0540-445. FIGS. 3 and 4 are perspective views of the FIGS. 1 and 2 embodiments, respectively, and they show the texture of the surfaces of the embodiments formed by the raised areas 16 surrounding the depressions 14 in FIG. 3 and the raised areas 26 surrounding the depressions 24 in FIG. 4. FIG. 5 is an enlarged cross-sectional or end view of the FIG. 1 (and FIG. 3) embodiment showing the two layers 30 and 40 that underlie the textured surface layer 12, 22 coextruded with that layer. The middle, non-exposed layer 30 and the bottom layer exposed layer 40 are made of a butane linear low density polyethylene.

In both the examples of FIGS. 1 and 2, the thickness of the layers is approximately as follows: the outer exposed layer is extruded at about 0.6 mils but with the foaming agent increased about three-fold to about 2 mils, the middle layer of butane is about 0.5 to 0.75 mils, and the inner exposed layer is also about 0.5 to 0.75 mils. The average combined thickness of the middle and inner layer is about 1.5 mils, which when combined with the outer textured layer (after expansion by foaming) yields an overall thickness of about 3.5 mils, as measured from the height of the raised sections adjacent to the surface depressions.

The thicknesses and the exact types of plastics used to form the various layers can vary significantly. For example, LDPE, LLDPE, PP, EVA and EMA are all materials that foam well and could be used to make materials with appropriate coefficients of friction and appropriate tear resistance, depending upon the particular requirements specified by a customer or other designer.

The embodiment of FIG. 2 is similar to the embodiment of FIG. 1 with regard to the number and thicknesses of the layers. In the embodiment of FIG. 2, however, the depressions are more elongated and narrower than in FIG. 1. For example the surface depression 24 in 2 has a length of about 0.3 inches, and a width of about 0.025 inches, yielding an aspect ratio of about 12 to 1. The surface layer of the FIG. 2 embodiment is comprised of raised striations of plastic that are longer and straighter than the raised areas of the FIG. 1 embodiment. As a result, the FIG. 2 embodiment is more easily torn. This tearability, however, may be useful in some instances where the surgical team wants to remove tubing or other components from a patient. In such instances, a cover that can be readily torn by hand may be afford an advantage over tougher covers, such as those containing a nonwoven surface layer.

Indeed, for certain specific kinds of surgeries, a combination of a tougher cover, such as the FIG. 1 embodiment, and a section of a more easily torn cover, such as that of the FIG. 2 embodiment, may be ideal. For example, because the materials of both FIGS. 1 and 2 are all plastic (without any nonwoven material), one or more windows may be cut out from a sheet made of the tougher FIG. 1 material, and a section of material made in accordance with FIG. 2 can by attached by heat sealing over (or under) the window cut from the tougher material.

Figure 6:
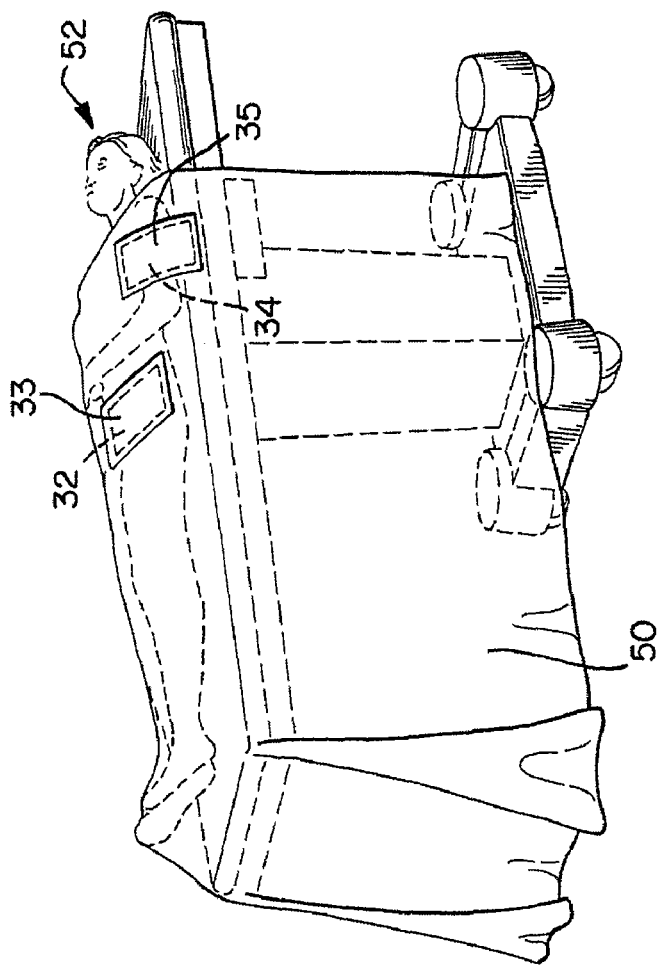
FIG. 6 is a perspective view of an exemplary patient drape made in accordance with the inventions claimed herein.

FIG. 6 shows a patient drape 50 covering most of a patient 52. Windows 32 and 34 have been cut from the drape 50, and patches 33 and 35, respectively, of a more easily torn material, such as that of the FIG. 2 embodiment discussed above, are place over and heat sealed to the outside surface of the drape. Alternatively, the patches could be heat sealed, or sealingly attached by other methods, to the inside surface of the drape 50.

The present invention has been described by reference to examples, which are presently considered to be the most practical and best embodiments. However, it is important to understand that the invention is not limited to the disclosed description or to the particular examples shown and described, but on the contrary, is intended to cover various modifications, improvements and equivalent arrangements that fall within the spirit and scope of the appended claims.

What is claimed is:

1. A surgical covering comprising: a sheet formed from a process selected from the group consisting of a blown film and a cast film process, the sheet having a plurality of layers, an outer exposed textured layer having a surface texture defined by laterally elongated depressions that are oval-like in shape and laterally elongated raised portions, at least one of the other layers of said plurality of layers being substantially solid and without through openings, and wherein the depressions are the result of the stretching and bursting of bubbles formed by said foaming agent as the plurality of layers leave an extrusion die.

2. A surgical covering in accordance with claim 1 wherein the depressions have lengths of between about 0.02 inches up and about 0.2 inches.

3. A surgical covering in accordance with claim 2 where the elongated oval-like depressions have a length to width ratio of about 5:1.

4. A surgical covering in accordance with claim 1 wherein the outer exposed textured layer is made of a material selected from the group consisting of linear low density polyethylene and low density polyethylene.

5. A surgical covering in accordance with claim 1 where in the outer exposed textured layer has a kinetic coefficient of friction against metal of at least about 0.36.

6. A surgical covering in accordance with claim 1 where in the outer exposed textured layer has a static coefficient of friction against metal of at least about 0.39.

7. A surgical covering in accordance with claim 1 wherein the outer exposed textured layer has a kinetic coefficient of friction, using the covering itself, of at least about 0.42.

8. A surgical covering in accordance with claim 1 where in the outer exposed textured layer has a static coefficient of friction, using the covering itself, of at least about 0.49.

9. A surgical covering in accordance with claim 1 wherein the overall thickness of the covering is between about 1 mil and about 4 mils, and the thickness of the outer exposed textured layer is between about 0.5 mils and about 2.0 mils.

10. A surgical covering in accordance with claim 1 wherein the depressions have lengths of up to about 0.5 inches.

11. A surgical covering in accordance with claim 1 wherein the outer exposed textured layer, when oriented in a vertical position, retains water droplets having a diameter of greater than approximately 1/16".

12. A surgical covering in accordance with claim 1 wherein the outer exposed textured, when oriented in a vertical position, retains water droplets having a diameter of greater than approximately 1/32".

13. A surgical covering in accordance with claim 1 wherein the outer exposed textured layer is non-glare.

14. A surgical covering in accordance with claim 1 wherein the outer exposed textured layer has a satin-like texture.

15. A surgical covering in accordance with claim 1 wherein the covering is readily tearable by hand without the use of tools in the direction of the length of the elongated oval-like depressions.

16. A surgical covering in accordance with claim 1 wherein the covering is readily tearable by hand without the use of tools or the use of excessive force in the direction of the length of the elongated oval-like depressions.

17. A surgical covering comprising:
a sheet with a first layer defining a plane, the first layer having an outer exposed textured surface defined by oval-like depressions elongated in the direction of the plane of the first layer and raised portions, and
a core layer, and
a third layer on a side of the core opposite the first layer, the core and the third layer being solid layers,
the core and third layers being co-extruded together with the first layer to form a single surgical covering, and the first layer being formed by use of a blowing agent forming bubbles that pop to create said depressions and said raised portions.

18. A surgical covering in accordance with claim 17 wherein at least one opening formed in said sheet is covered by a patch sealed to said sheet, said patch being readily tearable by hand to form a passageway through the at least one opening in the sheet of the surgical covering.

19. A surgical covering in accordance with claim 18 wherein material comprising the sheet is substantially more difficult to tear than the material comprising the patch.

20. A surgical covering comprising:
a sheet having at least two layers being co-extruded to form a single surgical covering;
the sheet having an outer exposed textured surface defined by a plurality of elongated oval-like depressions elongated in the direction of a plane defined by a first of said at least two layers and raised portions between the plurality of oval-like depressions, and
the outer exposed textured surface being capable of retaining liquid droplets having a diameter of greater than approximately 1/32", when the sheet is oriented in a vertical position;
the outer exposed textured surface having a kinetic coefficient of friction against metal of at least about 0.36; and,
the outer exposed textured surface being formed by the inclusion of a foaming agent in the extrusion process, and said foaming agent creating bubbles that pop to form said depressions and said raised portions.

\* \* \* \* \*